United States Patent [19]
Curtis et al.

[11] 3,933,798
[45] Jan. 20, 1976

[54] NOVEL BIS-PYRAZOLONE OXONOL DYES

[75] Inventors: Harris L. Curtis, Needham; James W. Foley, Andover, both of Mass.

[73] Assignee: Polaroid Corporation, Cambridge, Mass.

[22] Filed: Aug. 27, 1974

[21] Appl. No.: 500,842

[52] U.S. Cl. ........... 260/239.9; 260/240; 260/240.2
[51] Int. Cl.² ............ C07D 231/42; C07D 233/00; C07D 235/00; C07D 261/16
[58] Field of Search ..... 260/239.9, 240, 310, 240.2; 96/84 R, 84 A

[56] References Cited
UNITED STATES PATENTS

| | | |
|---|---|---|
| 2,621,125 | 12/1952 | Dormael et al. ........................... 95/8 |
| 2,944,901 | 7/1960 | Carroll .................................. 96/102 |
| 3,502,474 | 3/1970 | Tsuda et al. ............................. 96/84 |
| 3,795,519 | 3/1974 | Mlyazake et al. .................... 96/84 A |

*Primary Examiner*—Albert T. Meyers
*Assistant Examiner*—D. W. Robinson
*Attorney, Agent, or Firm*—Philip G. Kiely

[57] ABSTRACT

Novel, water-insoluble bis-pyrazolone oxonol dyes are provided wherein each pyrazolone nucleus carries an alkyl sulfonamidophenyl moiety on the 1-position nitrogen atom and an electron-withdrawing substituent on the 3-position carbon atom.

4 Claims, 2 Drawing Figures

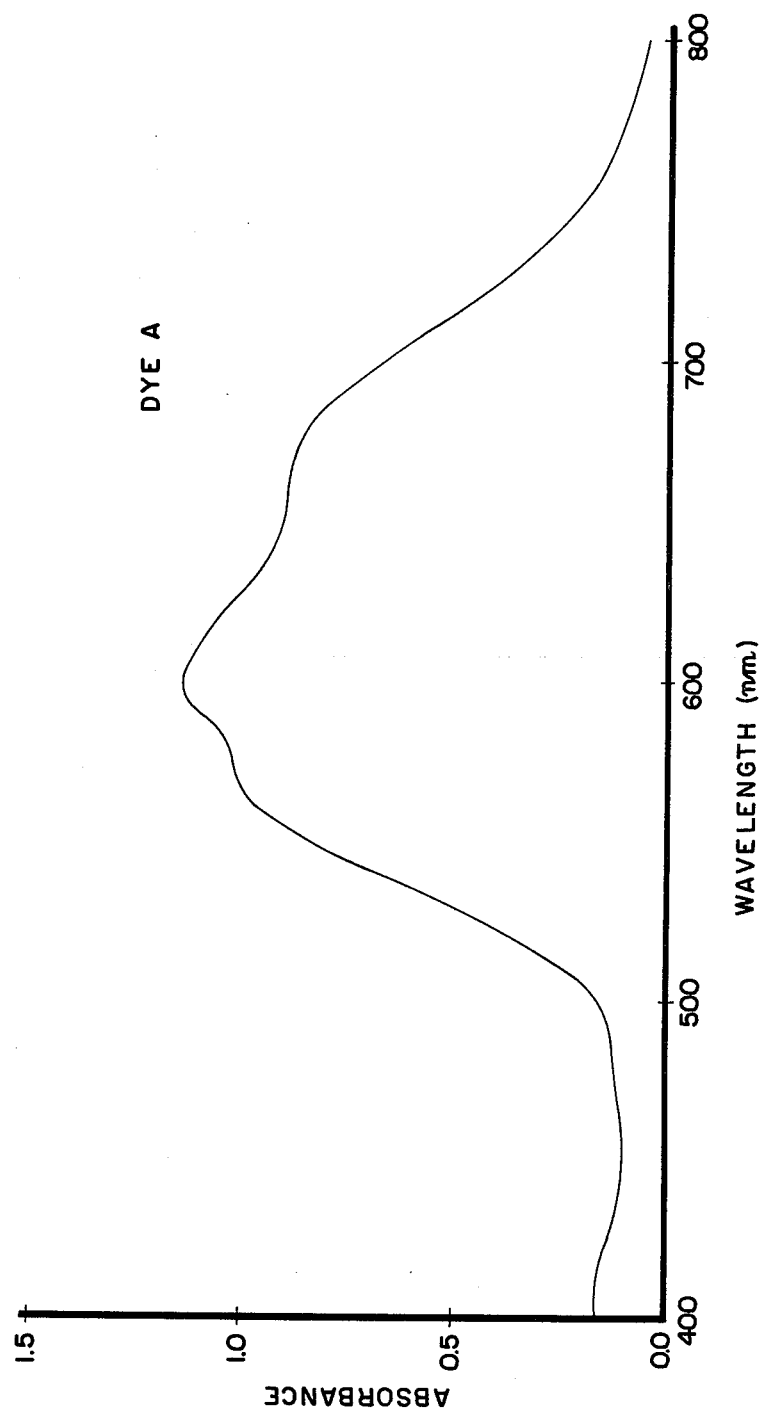
FIG. I

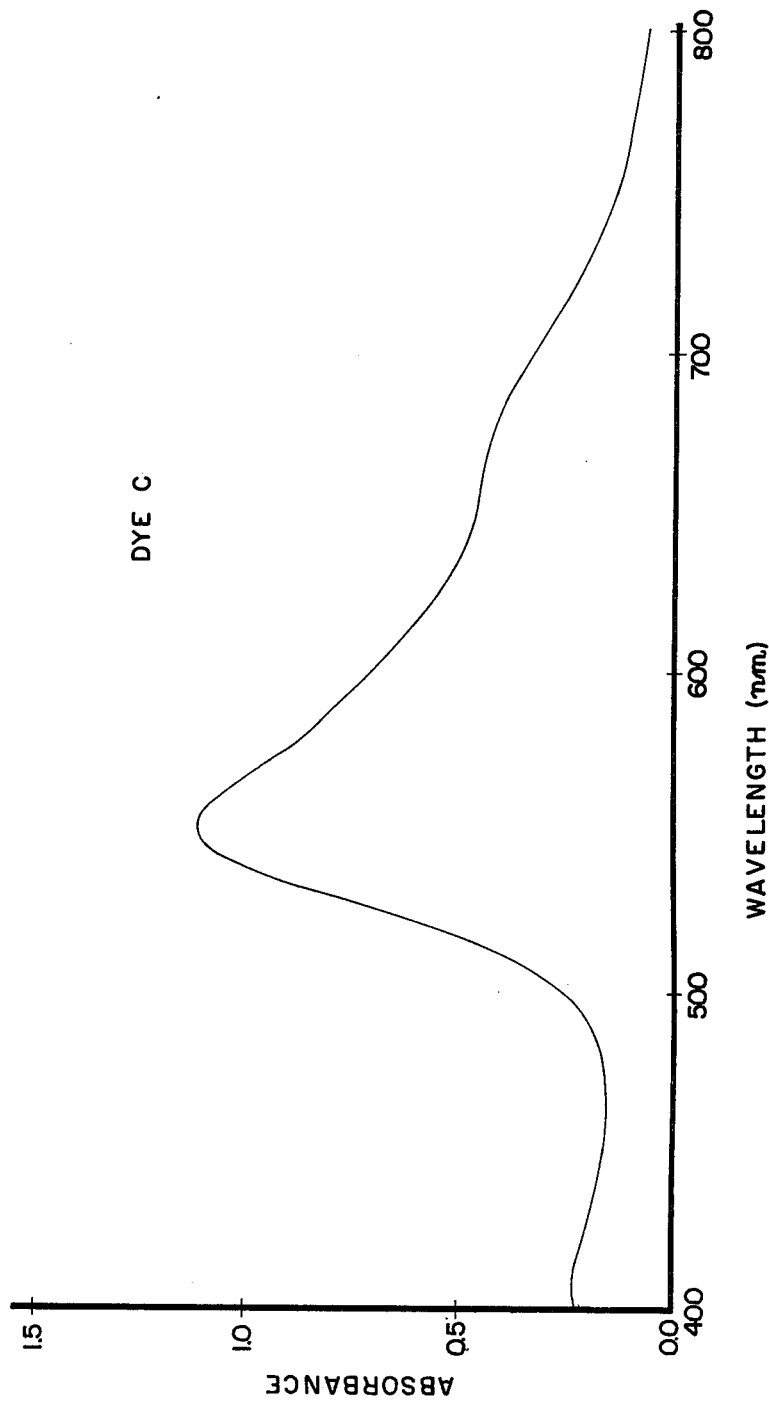

NOVEL BIS-PYRAZOLONE OXONOL DYES

BACKGROUND OF THE INVENTION

1. Field of the Invention

This invention relates to chemistry and, in particular, to novel bis-pyrazolone oxonol compounds useful as antihalation dyes in photographic products and processes.

2. Description of the Prior Art

Photographic light-sensitive elements are often provided with antihalation layers for the purpose of absorbing harmful reflected, scattered and/or diffused light which can adversely effect the quality of image reproduction. Such layers typically contain organic dyes possessing the desired spectral absorption properties distributed at a convenient coverage in a suitable polymeric hydrophilic colloid matrix. Since these dyes often have a deleterious effect on the light-sensitive layers used in the photosensitive element, it is important that these dyes be immobile and do not diffuse to the adjacent layers. Further, it is also generally necessary, particularly in films adapted for image reproduction by projection, that these dyes be rapidly and completely discharged or decolored (bleached) during the photographic processing steps to enable unhindered viewing of the developed image.

Although several pyrazolone dyes and, particularly bis-pyrazolone oxonol dyes, have previously been proposed as antihalation dyes in photographic products and processes (see, for example, U.S. Pat. Nos. 2,621,125; 3,502,474; and 3,795,519), none have satisfactorily met all of the desired requirements; in particular, they either bleach too slowly and/or are mobile in gelatin matrices.

A class of bis-pyrazolone oxonol dyes has now been found which does not possess the above-mentioned deficiencies of the prior art and which dyes are particularly suited as antihalation dyes in photographic products and processes.

BRIEF SUMMARY OF THE INVENTION

In accordance with this invention, novel bis-pyrazolone oxonol dyes are provided wherein each of the two pyrazolone nuclei carry an alkyl sulfonamidophenyl moiety on the 1-position nitrogen atom and an electron-withdrawing substituent on the 3-position carbon atom. The dyes of the present invention are substantially water-insoluble and less mobile in gelatin matrices than dyes of similar structure without said alkyl sulfonamidophenyl moiety. In preferred embodiments, the dyes of the present invention are superior to known antihalation dyes in that they are relatively innocuous to photographic silver halide emulsions, form stable dispersions in gelatin and bleach rapidly in alkaline processing compositions.

BRIEF DESCRIPTION OF THE DRAWINGS

FIGS. 1 and 2 are graphic representations of the spectral absorption curves for gelatin dispersions of two antihalation dyes of the present invention.

DETAILED DESCRIPTION OF THE INVENTION

The novel bis-pyrazolone oxonol dyes of the present invention may be represented by the following general formula:

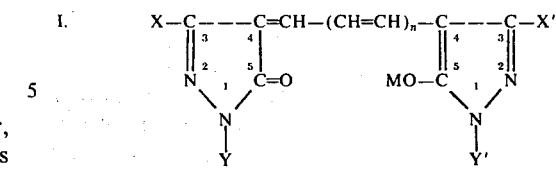

wherein X and X' are the same and represent an electron-withdrawing substituent, e.g., ester, amide, cyano, etc.; Y and Y' are the same and represent an alkyl sulfonamidophenyl moiety, e.g., p-n-pentylsulfonamidophenyl, p-n-hexylsulfonamidophenyl, etc.; M is hydrogen or a cation, e.g., an inorganic cation such as an alkali metal ion (i.e., $Na^-$, $K^-$, etc.) or an organic onium ion such as pyridinium; and n is 0, 1 or 2.

All formulae set forth herein, including the appended claims, are intended to be only illustrative of one form of the actual structure of the depicted compound. The "oxonol" grouping contained within the structural formulae of the compounds of the present invention is believed to undergo tautomeric (ketol-enol) rearrangements and, therefore, may actually exist in a variety of structures, the extremes of which may be represented, for example, by the formulae:

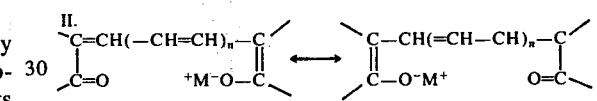

It is to be understood, therefore, that all such formulae contained in this specification and the appended claims represent the depicted structure and any tautomeric equivalent thereof.

Bis-pyrazolone oxonol dyes of the prior art generally exhibit relatively high water solubility. In contrast to these prior art dyes, the alkyl sulfonamido groups of the N-phenyl substituents of each pyrazolone nucleus render the dyes of this invention substantially water-insoluble and, therefore, immobile (i.e., nondiffusible) in the hydrophilic colloid in which they are incorporated to form an antihalation layer in a photographic element.

The alkyl sulfonamidophenyl groups depicted as Y and Y' in Formula I may each be represented by the formula:

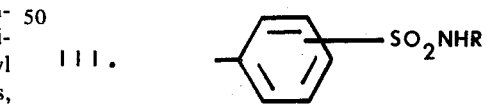

wherein R is an alkyl group. The alkyl portion R of the alkyl sulfonamidophenyl group should be of sufficient size to provide the desired immobilizing effect, yet not so large as to adversely effect the dye's ability to form a fine dispersion that is stable in the hydrophilic colloid. Alkyl groups having from 3 to 8 carbon atoms are contemplated as being suitable for providing the R moiety, and straight chain alkyl groups containing 5 carbon atoms in the chain, i.e., n-pentyl groups, have been found to be particularly useful. The phenyl nucleus may also include substituents other than the alkyl sulfonamido group such as, for example, halogen, alkyl, alkoxy, etc. Also, as indicated in Formula III, the alkyl sulfonamido group may be in various positions on the phenyl nucleus, i.e., in ortho-, para- or meta-position.

X and X' in Formula I represent electron-withdrawing substituents on the 3-position carbon atom of each pyrazolone nucleus. The term "electron-withdrawing substituent" is herein intended to designate those substituents known in the dye art as "electronegative" or "electron-attracting" groups. Such electrophilic groups have been found to contribute to the fast bleaching properties of the present dyes, when said dyes are contacted with an alkaline photographic processing composition. As examples of electrophilic substituents contemplated by X and X', mention may be made of any of the electronegative substituents conventionally used in the dye art, e.g., cyano, nitro, sulfonyl, etc., and particularly those electronegative substituents containing carbonyl groups such as esters and amides.

Dyes of Formula I wherein X and X' represent ester groups, particularly 2-alkoxy or 2-hydroxy ethoxy carbonyl groups, have been found to provide especially desirable antihalation dyes in accordance with the present invention. Such ester groups may be represented by the formula:

IV.

wherein Z is hydrogen, hydroxy or lower alkoxy, e.g., methoxy, ethoxy, etc., and $m$ is the integer 2 or 3. The value of $m$ above, i.e., the length of the alkylene chain in the ester substituent, has a marked effect on the water solubility of the resultant dye compound. As the value of $m$ increases, the water solubility and, therefore, the mobility of the dye in a hydrophilic colloid layer decreases. For example, prior art dyes analogous to those of Formula I with the 1-N-phenyl substituents but without the alkyl sulfonamido substituent on each phenyl nucleus and having $m$ values of 1 or 2 are quite water-soluble and mobile in gelatin, whereas those dyes in which $m$ is 5 are water-insoluble and immobile.

However, it has been found that the rate at which the dye bleaches to a decolored state when treated with an alkaline photographic processing composition also decreases as $m$ increases. Since, in preferred photographic applications, antihalation dyes are required to bleach out rapidly during the processing steps, the length of the alkylene chain must necessarily be kept short, for example, an ethylene chain ($m=2$) is preferable. In the prior art, this requirement of a short alkylene chain in ester substituents has led to dyes with unacceptably high mobility. The superior immobilizing properties of the alkyl sulfonamidophenyl groups in the dyes of the present invention, however, allow for the utilization of the desirable lower alkyl ester substituents as well as other more rapid-bleaching (and water-solubilizing) substituents in the bis-pyrazolone oxonol dye structure without sacrificing the desired immobility. Particularly rapid-bleaching but immobile dyes of Formula I are provided when Z in Formula IV is hydroxy (—OH) or lower alkoxy (—OCH$_3$, —OC$_2$H$_5$, etc.). It should be noted that the selection of Z may also affect the light absorption characteristics of the dye when dispersed in gelatin. For example, comparing the absorption curves for Dyes A and C in FIGS. 1 and 2, it can be seen that Dye C with Z as —OH absorbs more green light than corresponding Dye A with Z as —H.

The value of $n$ in Formula I, i.e., the length of the methine linkage between pyrazolone nuclei, may also determine the light-absorbing or color properties of the resultant dye. In general, pentamethine dyes of Formula I (i.e., $n=2$) are blue-cyan, trimethine dyes of Formula I (i.e., $n=1$) are magenta and monomethine dyes of Formula I (i.e., $n=0$) are yellow. Pentamethine bis-pyrazolone oxonol dyes of Formula I are the most preferred for use as antihalation dyes in the photographic products and processes described hereinafter.

The superior immobilizing effect of the alkyl sulfonamido groups on the 1-N-phenyl nuclei of the present dyes will be further illustrated by the following example:

EXAMPLE I

Bis-1,5-[3-(2-methoxyethoxy)carbonyl-1-(p-N-n-pentylsulfonamidophenyl)-2-pyrazolin-5-one]pentamethine oxonol (i.e., Dye B in Example II hereinafter) and bis-1,5-[3-(2-methoxyethoxy)carbonyl-1-phenyl-2-pyrazolin-5-one]pentamethine oxonol, an identical dye without the n-pentylsulfonamido groups (hereinafter designated B') were each dispersed in gelatin. Similarly, bis-1,5-[3-(2-hydroxyethoxy)carbonyl-1-(p-N-n-pentylsulfonamidophenyl)-2-pyrazolin-5-one]pentamethine oxonol (i.e., Dye C in Example II hereinafter) and bis-1,5-[3-(2-hydroxyethoxy) carbonyl-1-phenyl-2-pyrazolin-5-one]pentamethine oxonol, an identical dye without the n-pentylsulfonamido groups (designated C') were also dispersed in gelatin.

The dispersions were cubed and washed in distilled water for about 1.3 hours. The optical density of the filtered wash water was measured and the values used to compare the relative mobilities of the dyes in gelatin. Table 1 below summarizes the results:

TABLE 1

| Dye | Optical Density of Wash Water at 600 m$\mu$ |
|-----|--------------------------------------------|
| B   | 0.01 |
| B'  | 1.63 |
| C   | 0.02 |
| C'  | 2.00 |

It can be clearly seen from the densities in Table 1 that the dyes without the immobilizing n-pentylsulfonamido groups on each 1-N-phenyl nucleus were readily washed out of the gelatin dispersion into the wash water whereas the dyes with the n-pentylsulfonamido groups of this invention were retained in the dispersion with a relatively insignificant amount appearing in the wash water.

When treated with an alkaline solution, such as a photographic developing composition, the water-solubility of the dyes of Formula I substantially increases, most likely due to the ionization of the alkyl sulfonamido group (—SO$_2$N$^-$R). Hence, the dyes of the present invention become more mobile in the hydrophilic colloid of the antihalation layer and may be dissolved out of the hydrophilic colloid layer during the photographic processing step subsequent to exposure of the film unit. In addition, this increased solubility is accompanied by a more rapid bleaching of the dye when the processing solution contains sodium sulfite (Na$_2$SO$_3$) and sodium hydroxide (NaOH) as the principal bleaching agents.

Dyes of the present invention may be obtained from corresponding pyrazolone compounds according to general procedures known in the art, for example, as outlined in British Pat. Nos. 506,385 and 646,125 and U.S. Pat. No. 3,502,474. Such procedures typically comprise a condensation reaction between 2 mols of the appropriate pyrazolone compound having an active methylene group in the pyrazolone ring and 1 mol of glutacondialdehyde dianil in a solvent, such as an alcohol or dimethyl sulfoxide, in the presence of a condensing agent such as triethylamine, pyridine, etc. The 1-(p-N-alkylsulfonamidophenyl)-substituted pyrazolone intermediates employed in the hereindescribed syntheses may also be prepared in a known manner, such as by reacting a diethyl acetyl succinate with an appropriate diazonium compound according to known procedures in the art, for example, as disclosed in British Pat. No. 585,780.

The following nonlimiting examples will serve to illustrate the preparation of dyes within the scope of this invention:

EXAMPLE II

DYE A

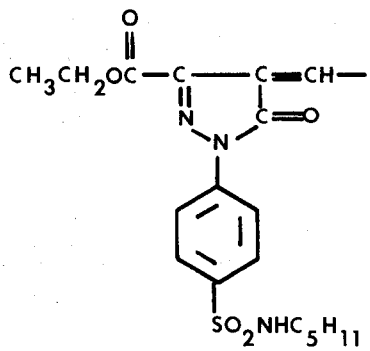

Bis-1,5-[3-carbethoxy-1-(p-N-n-pentylsulfonamidophenyl)-2-pyrazolin-5-one]-pentamethine oxonol The above dye was prepared according to the following procedure:

153 grams (0.4 mols) of 3-carbethoxy-1-(p-N-n-pentylsulfonamidophenyl)-2-pyrazolin-5-one, 51.5 grams (0.2 mols) of glutaconaldehyde dianil hydrochloride, and 72 grams (0.7 mols) of triethylamine were dissolved in 400 ml. of dry DMSO. The reaction mixture was stirred at room temperature for 2 hours and then precipitated into 6 liters of ice water containing 720 ml. of concentrated HCl. The brown precipitate was isolated by vacuum filtration and was washed with water until the washings were neutral. The solid Dye A was then dried under vacuum.

To form the preferred sodium salt form of Dye A, 150 grams of the dry Dye A was stirred with 600 grams of sodium bicarbonate in 2 liters of 2B ethanol for about 1 hour. The entire mixture was filtered; the residual sodium bicarbonate was washed with acetone to dissolve the small amount of product which crystallized from the ethanol solution. The dye was crystallized from 750 ml. of 2,2,2-trifluoroethanol to give 55 grams of crystals.

The very crystalline sodium salt product gave a melting point of 220° C. and an elemental analysis as follows:

|  | % of Element | | | | | |
|---|---|---|---|---|---|---|
|  | C | H | N | O | S | Na (by diff.) |
| Found | 55.11 | 5.75 | 9.86 | 18.93 | 7.52 | 2.83 |
| Theory | 55.24 | 5.71 | 9.95 | 18.93 | 7.59 | 2.78 |

The pyrazolone starting compound employed in the above synthesis was prepared as follows:

59 grams (0.24 mols) of N'-n-pentylsulfanilamide was suspended in a solution containing 200 ml. of water and 60 ml. of concentrated HCl. The solution was cooled to 5° C. and was stirred mechanically. To this solution was added dropwise an aqueous solution of 16.9 grams (0.24 mols) sodium nitrite. Stirring was continued for an additional 15 minutes; this solution was then added portionwise to a stirred, cold solution of 52 grams (0.24 mols) of diethylacetylsuccinate and 400 ml. of pyridine. The resulting solution was allowed to come to room temperature and was then heated on a steam bath overnight (a brown oil precipitated soon after heating was begun). The mixture was concentrated under vacuum to an oil. The oil was added to 4 liters of 5% aqueous HCl; a tan solid formed. The solid was collected, washed with distilled water, and dried. This material was used without further purification and NMR analysis indicated the product to be about 80% pure.

Dye B shown below was also prepared following essentially the same procedure employed in the preparation of Dye A with 3-(2-methoxy ethoxy)carbonyl-1-(p-N-n-pentylsulfonamidophenyl)-2-pyrazolin-5-one as the pyrazolone starting compound:

DYE B

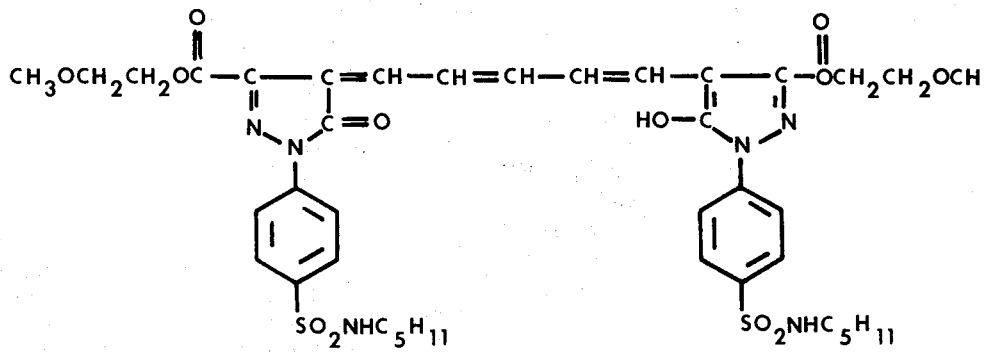

Bis-1,5-[3-(2-methoxy ethoxy)carbonyl-1-(p-N-n-pentylsulfonamidophenyl)-2-pyrazolin-5-one]-pentamethine oxonol The Dye B product gave a melting point of about 200° C. Following a similar procedure with 3-(2-hydroxy ethoxy)carbonyl-1-(p-N-n-pentylsulfonamidophenyl)-2-pyrazolin-5-one as the pyrazolone starting compound, a Dye C product, having a melting point of about 180° C., was also prepared:

DYE C

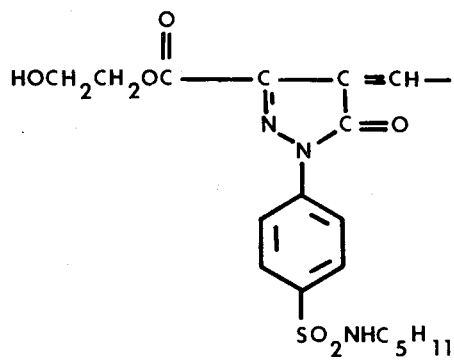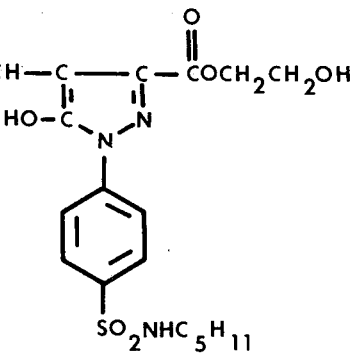

Bis-1,5-[3-(2-hydroxy ethoxy)carbonyl-1-(p-N-n-pentylsulfonamidophenyl)-2-pyrazolin-5-one]-pentamethine oxonol Dyes of the present invention may also be prepared via transesterification (ester interchange) reactions employing as a catalyst a porous absorbent such as a zeolitic material which has the properties of a molecular sieve. (See, for example, U.S. Pat. No. 3,328,439). Accordingly, the following nonlimiting example illustrates the preparation of Dye B from Dye A by such a procedure:

EXAMPLE III 12 grams of Dye A was suspended in 240 ml. of 2-methoxyethanol with 48 grams of a molecular sieve material (a sodium cation aluminosilicate marketed under the designation M-514, Type 4A by Davison Division, W. R. Grace Co.). The reaction mixture was stirred for one hour at 85° C. and then the molecular sieve material was slowly filtered off. The 2-methoxyethanol was evaporated off to form an oil which was recrystallized from trifluoroethanol. The purified product gave the following representative elemental analysis:

|  | % of Element | | | |
|---|---|---|---|---|
|  | C | H | N | S |
| Found | 54.29 | 5.67 | 9.27 | 7.07 |
| Theory | 54.10 | 5.61 | 9.21 | 6.84 |

Following essentially the same molecular sieve transesterification procedure as set forth immediately above, Dye C was also prepared from Dye A by using ethylene glycol instead of 2-methoxyethanol.

As previously indicated, the employment of antihalation dyes and layers in photographic elements is well established in the art and the dyes of this invention are contemplated as being useful wherever prior art dyes have been used for this purpose. Typically, antihalation dyes of this invention may be disposed in a separate hydrophilic colloid layer of the film unit, usually intermediate a photosensitive silver halide emulsion layer and the film base support. The selected dye or mixture of dyes may be dispersed as a solution or in particulate form in a coating solution containing, for example, gelatin as the hydrophilic colloid binder and the resultant coating solution may be subsequently applied to a support.

Illustrative film units in which the dyes of the present invention are advantageously employed are described, for example, in the copending application of Edwin H. Land, Ser. No. 383,261, filed July 27, 1973. Said film units comprise, in the order in which incident light passes therethrough, at least an additive multicolor screen, a photosensitive silver halide emulsion layer and an antihalation layer in which the present dyes may be incorporated, and are adapted to form a multicolor projection image by silver diffusion transfer techniques.

As described in detail in said application, exposure of the silver halide layer is accomplished through the screen which possesses optical filter elements selectively transmitting to the underlying photosensitive silver halide layer predetermined portions of the electromagnetic radiation incident thereon, e.g., red, green and blue light. Photographic processing of the thus-exposed silver halide layer with an alkaline processing composition results in the diffusion transfer and deposit of silver in a superposed image-receiving layer of the film unit as a function of the degree of exposure of silver halide behind each filter element. The resultant silver image in the image-receiving layer may then serve to modulate the quantity of light passing through the filter elements in the reverse direction during projection through a transparent support.

In preferred film units of the above-described type, the image-receiving layer is intermediate the silver halide layer and the multicolor screen and remains in position as part of an integral film unit before, during and after the formation of the image. The antihalation layer is disposed next adjacent the photosensitive layer on the side opposite the screen and serves to prevent the reflection or back-scattering of incident light which has passed through the thin photosensitive layer. The light-absorbing properties of the novel antihalation dyes of this invention, when incorporated in such antihalation layers, effectively eliminate the exposure of silver halide grains in the photosensitive layer other than those within the intended path of incident radiation, thereby providing improved color separation and rendition in the final image. As previously mentioned, FIGS. 1 and 2 graphically show the absorption properties of gelatin dispersions of representative dyes of the present invention, i.e., Dyes A and C, respectively.

The dyes of the present invention are preferably dispersed in a processing composition permeable layer to serve their light-absorbing function during exposure of the film unit, and are then discharged and/or bleached to a substantially nonabsorbing form when the processing composition is applied and permeates the layers of the film unit prior to the viewing of the developed image. As set forth in the aforementioned application, other arrangements and methods are also available for dissociating the antihalation layer from the film unit subsequent to photoexposure, for example, by stripping the layer from the film unit, and additional layers may be optionally included in the film units such as, for example, separate layers retaining processing reagents, barrier layers, protective layers, support layers and the like.

Since certain changes may be made in the hereindescribed subject matter without departing from the scope of the invention herein involved, it is intended that all matter contained in the above description and examples be interpreted as illustrative and not in a limiting sense.

What is claimed is:

1. A compound of the formula:

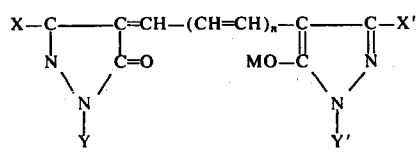

wherein X and X' are the same and each represents an ester group of the formula:

wherein Z is hydrogen, hydroxy or lower alkoxy and $m$ is the integer 2 or 3; Y and Y' are the same and represent an alkyl sulfonamidophenyl group of the formula:

wherein R is an alkyl group having from 3 to 8 carbon atoms, the —SO$_2$NHR group being in ortho-, para- or meta-position on the phenyl nucleus; M is hydrogen, Na$^+$, K$^+$ or pyridinium; and $n$ is 0, 1 or 2.

2.

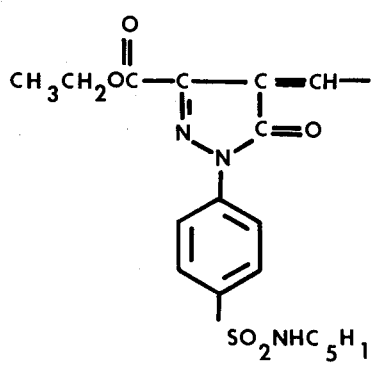 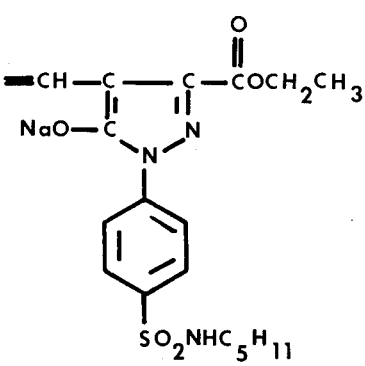

3.

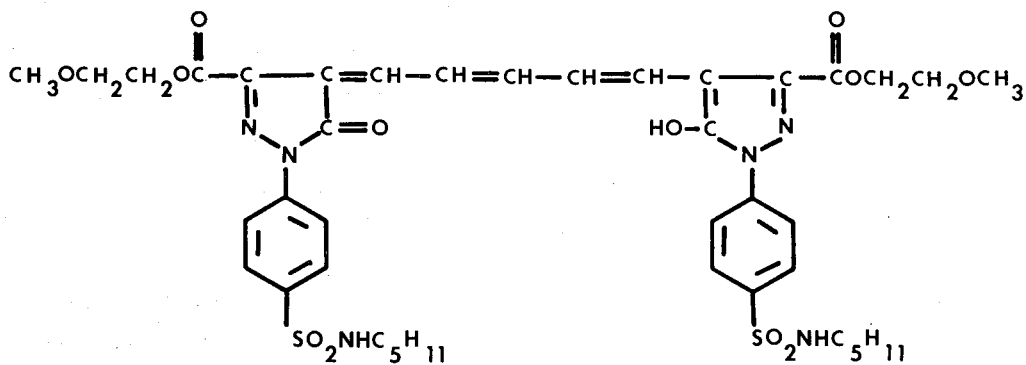

4.

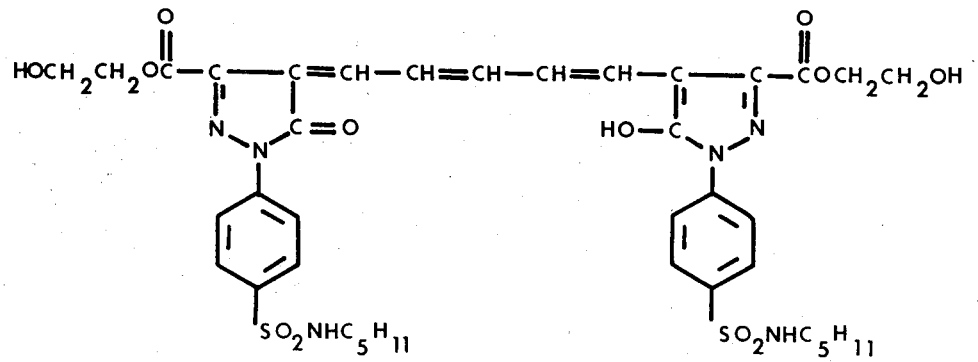

* * * * *